US008562967B2

(12) United States Patent
Hinderer et al.

(10) Patent No.: US 8,562,967 B2
(45) Date of Patent: Oct. 22, 2013

(54) STABLE LIQUID FORMULATIONS OF G-CSF

(75) Inventors: Walter Hinderer, Rodgau (DE); Heinz Lubenau, Neustadt (DE)

(73) Assignee: Biogenerix AG, Ulm (DE)

( * ) Notice: Subject to any disclaimer, the term of this patent is extended or adjusted under 35 U.S.C. 154(b) by 161 days.

(21) Appl. No.: 12/675,776

(22) PCT Filed: Aug. 27, 2008

(86) PCT No.: PCT/EP2008/007012
§ 371 (c)(1),
(2), (4) Date: Apr. 16, 2010

(87) PCT Pub. No.: WO2009/027076
PCT Pub. Date: Mar. 5, 2009

(65) Prior Publication Data
US 2010/0216698 A1    Aug. 26, 2010

(30) Foreign Application Priority Data

Aug. 27, 2007  (DE) .......................... 10 2007 040 932
Aug. 27, 2007  (EP) ..................................... 07016763

(51) Int. Cl.
| A61K 45/00 | (2006.01) |
| A61K 47/02 | (2006.01) |
| A61K 47/12 | (2006.01) |
| A61K 38/19 | (2006.01) |
| C07K 14/00 | (2006.01) |

(52) U.S. Cl.
USPC ............................ 424/85.1; 530/351; 514/7.6

(58) Field of Classification Search
None
See application file for complete search history.

(56) References Cited

U.S. PATENT DOCUMENTS

| 5,284,656 | A * | 2/1994 | Platz et al. .................... 424/435 |
| 5,503,827 | A | 4/1996 | Woog et al. |
| 5,919,443 | A | 7/1999 | Michaelis et al. |
| 5,919,757 | A | 7/1999 | Michaelis et al. |
| 2008/0026046 | A1 * | 1/2008 | Skufca et al. ................. 424/450 |
| 2009/0247450 | A1 | 10/2009 | Mack |

FOREIGN PATENT DOCUMENTS

| DE | 202007018618 | | 1/2006 | |
| DE | 202006020194 U1 * | | 6/2007 | ............. A61K 38/19 |
| EP | 0 373 679 | | 6/1990 | |
| EP | 0 988 861 | | 3/2000 | |
| EP | 1 060 746 | | 12/2000 | |
| EP | 1 129 720 | | 5/2001 | |
| EP | 1 988 913 | | 1/2007 | |
| WO | WO 87/ 01132 | | 2/1987 | |
| WO | WO 93/03744 | | 3/1993 | |
| WO | WO 94/ 14465 | | 7/1994 | |
| WO | WO 94/14466 | | 7/1994 | |
| WO | WO 04/001056 | | 12/2003 | |
| WO | WO 2005/039620 | | 5/2005 | |
| WO | WO 2005/042024 | | 5/2005 | |
| WO | WO 2007/099145 | | 9/2007 | |

OTHER PUBLICATIONS

Entry from the European Patent Office , related to WO2007099145, accessed Jun. 5, 2012.*
European Medicines Agency Assessment Report for RatioGrastim, Doc Ref EMEA/502481/2008.
Extract from AHFS—Drug Information (2001) "Filgrastim", pp. 1454-1463.
Extract from "Rote Liste", 2005, ECV Edition Cantor Verlag, Aulendorf, pp. 51030-51036.
Herman et al., "Formulation, Characterization, and Stability of Neupogen (Filgrastim), a Recombinant Human Granulocyte-Colony Stimulating Factor"; Perlman and Wang, Eds. (1996), pp. 303-328.
Translation of International Report on Patentability issued Apr. 8, 2010 for PCT/E2008/007012.
Opposition against EP 1 988 913 B1 by Teva Pharmaceuticals Industries Ltd., Apr. 22, 2009.
Opposition against EP 1 988 913 B1 by Hospira UK Ltd., Jan. 25, 2010.
Opposition against EP 1 988 913 B1 by Sandoz AG, Jan. 20, 2010.
Opposition against EP 1 988 913 B1 by ratiopharm GmbH and CT Arzneimittel GmbH, Apr. 23, 2009.
English translation of the opposition petition by ratiopharm GmbH and CT Arzneimittel GmbH in opposition to proceedings concerning European patent EP 1 988 913 B1, Apr. 23, 2009.
English translation of further petition by ratiopharm GmbH and CT Arzneimittel GmbH in opposition to proceedings concerning European patent EP 1 988 913 B1, Apr. 23, 2009.
Petition in Utility Model Cancellation Proceedings concerning German Utility Model DE 20 2007 018 618 U1, Sep. 23, 2009.
English translation of petition in Utility Model Cancellation Proceedings concerning German Utility Model DE 20 2007 018 618 U1, Jan. 25, 2010.
Examination report in parallel European patent application No. 08 785 714.0, Apr. 8, 2010.
English translation of Examination report in parallel European patent application No. 08 785 714.0, Apr. 8, 2010.
Examination report in German priority patent application DE 10 2007 040 932.1, Aug. 7, 2008.
English translation of Examination report in German priority patent application DE 10 2007 040 932.1, Aug. 7, 2008.

(Continued)

*Primary Examiner* — Elly-Gerald Stoica
(74) *Attorney, Agent, or Firm* — MH2 Technology Law Group, LLP

(57) ABSTRACT

Provided are pharmaceutical liquid formulations of G-CSF, which are stable over a long time period and substantially free of excipients, as well as ready-to-use syringes containing such formulations and corresponding kits.

25 Claims, No Drawings

(56) References Cited

OTHER PUBLICATIONS

Declaration of Dr. Walter Hinderer submitted in European Patent Application 08785714.0 with Exhibit A: (a comparative analysis of G-CSF monomer and dimer formation following storage for four weeks at 40° C.) and Exhibit B: (Assessment Report on Ratiograstim).

Communication pursuant to Article 94(3) EPC dated May 21, 2012 from European Patent Application No. 08 785 714.0-1219.

Ratiopharm Press Release: "Biosimilar Ratiograstim received EMEA approval", Sep. 2008.

* cited by examiner

STABLE LIQUID FORMULATIONS OF G-CSF

CROSS-REFERENCE TO RELATED APPLICATIONS

This application is a U.S. National Stage application of PCT/EP2008/007012, filed 27 Aug 2008, the entire disclosure of which is hereby incorporated herein by reference.

BACKGROUND OF THE INVENTION

1. Field of the Invention

Objects of the present invention are stable, aqueous liquid formulations of G-CSF, substantially consisting of G-CSF and a sugar alcohol, a surfactant, a buffer substance at a pH value of about 4.1 to 4.4, and optionally also amino acids and/or glycerol and/or carbohydrates and/or preservatives.

2. Description of Related Art

Many of the hitherto known dosage forms for protein agents have disadvantages. For instance, certain preparations contain pharmaceutical additives or excipients that cannot readily be categorized as harmless from a medical point of view. Due to their origin and physico-chemical properties, polymers and proteins bear a certain risk potential with respect to their suitability as pharmaceutical additives. Proteins of human or animal origin as well as proteins obtained from cell cultures bear a potential residual risk of viral contaminations. Due to their antigenic properties, other protein-like contaminations, which are difficult to detect analytically, can also trigger immunological reactions in humans. Moreover, proteins of animal origin can trigger immunological reactions in humans due to their species-specific properties in general. Long-term reactions upon reapplication of such proteins at a later point in time are also possible.

The admixture of compounds having a high molecular weight can also be problematic. Polymers can be accumulated in the body due to their high molecular mass and can therefore remain in the body for a long time, in case there is no biodegradation. This is, in particular, to be feared in case of subcutaneous application, as removal and distribution via the bloodstream is much more delayed in comparison to intravenous application. Depending on the molar mass, polymers can also have antigenic properties. Furthermore, the purity of polymers is difficult to ensure due to the catalysts used for production or due to the presence of monomers and other polymer fragments. The use of polymers in liquid pharmaceutical dosage forms is thus to be avoided as far as possible, in particular with subcutaneously applicable dosage forms.

Furthermore, it is known from the literature that particularly non-glycosylated forms of G-CSF, when compared to glycosylated G-CSF obtained from CHO cells, are extremely unstable owing to oxidation and/or aggregation. It is therefore extremely difficult to stabilize non-glycosylated forms of G-CSF and specifically selected measures are required to formulate said molecule into a stable dosage form.

The use of surfactants for stabilizing G-CSF is principally to be avoided from a medical point of view as said surfactants may trigger local irritations. Formulations having a very low pH value, in particular in case of a subcutaneous application, can also lead to local incompatibilities in patients, e.g. pain and local tissue irritation, as said pH value lies below the physiological range from pH 7.0 to 7.5 that is present in the tissue.

The recently published international application WO 2005/042024, similarly to the teachings of EP 373 679, teaches a way of obtaining stable pharmaceutical compositions of G-CSF by keeping said compositions, inter alia, free of surfactants and, in accordance with the compositions described in the Examples, by providing the buffer at a very low concentration. There are no indications given with respect to the acceptability of the medicaments described therein.

In the European patent application EP 1 129 720, preparations of G-CSF having a pH value in the range from 5 to 8 are described, wherein sulfate is supposed to stabilize the G-CSF contained in the preparation. Again, there are no indications given with respect to the acceptability of the G-CSF preparations described therein.

SUMMARY OF THE INVENTION

The problem underlying the present invention is to provide a liquid dosage form for G-CSF which does not show the above-described disadvantages of the hitherto known dosage forms. In particular, the pharmaceutical preparation should be stable over a long time period as well as physiologically acceptable. It should, in particular, be suitable for self-application by patients and it should be characterized by the capability to avoid undesired irritations of the skin and pain at the injection site often occurring along with the self-application of medicaments by means of an injection or infusion.

This problem is solved by the embodiments characterized in the claims and is illustrated in the following embodiments. In particular, the present invention relates to stable, aqueous liquid formulations of G-CSF substantially consisting of G-CSF and a sugar alcohol, a surfactant at a concentration of about 0.04 to 0.06 mg/ml, acetate at a concentration of about 5 to 20 mM as a buffer substance at a pH value of about 4.1 to 4.4. Optionally, amino acids and/or glycerol and/or carbohydrates and/or preservatives can be used. Furthermore, the liquid formulation according to the present invention can contain further pharmaceutically conventional excipients. However, the absence of said and/or other excipients is preferred.

In the international application WO 94/14466, in general, storage-stable aqueous pharmaceutical preparations of G-CSF are claimed that are supposed to be stable at a pH value within the range of 3.5 to 5 and 7 to 8 with the use of different buffer systems. However, only liquid G-CSF preparations with phosphate buffer are tested for their storage-stability, while individual experimental preparations with other buffers were tested only after short mechanical stress, i.e. turbidity for the occurrence of turbidities in the samples.

In the process of experiments conducted within the scope of the present invention it had to be assessed that the G-CSF solutions that had been indicated with acetate buffer in the Examples of WO 94/14466, in particular formulation 4 with 10 mM acetate and a pH value of 4.5, do not have the desired stability because critical values for the presence of aggregates and oxidized forms of G-CSF had been determined. Accordingly, it was at first assumed that, as already illustrated in EP 0 373 679, a pH value of more than 4.0 would result in the formation of aggregates and that a liquid formulation of G-CSF having a pH value of improved physiological acceptability could not be achieved using the otherwise preferred acetate buffer system.

In the international application WO 2005/039620, G-CSF liquid formulations of the composition 0.6 mg/ml G-CSF, 10 mM acetate buffer, 0.004% (w/v) Tween 80 and 5% (w/v) D-sorbitol having a pH value of 4.0 and 4.2 were used as comparative formulations in studies for the stability of G-CSF formulations under impact of mechanical stress and after freezing and thawing of G-CSF formulations with succinate buffer having a pH value of 5.0 and 0.02% (w/v) Tween 20. According to these studies, the G-CSF formulations with acetate buffer were less stable, so that it did not appear sensible to further study such acetate-buffered compositions, let alone to consider them as candidate medicaments.

In contrast thereto, in the process of experiments conducted within the scope of the present invention, advantageous properties of acetate-buffered G-CSF formulations having a pH>4.0 with respect to stability at storage temperatures in a refrigerator and at 40° C., i.e. in the range of body temperature, were surprisingly found as well as a surprisingly good acceptability in patients, as less skin irritations occurred in comparison to commercially available medicaments.

In particular, it was found that, in the sense of the present invention, by combining acetic acid and acetate, respectively, as a buffer substance and a surfactant such as polysorbate 80, each at a specific concentration and in the presence of a sugar alcohol such as sorbitol, and by adjusting the pH value to about 4.2±0.15, a stable liquid formulation of G-CSF is obtained, which conveys to the G-CSF molecules the stability required for their suitability as a medicament, is well tolerable and additionally allows for an almost complete prevention of symptoms that can often be observed at the injection site when administering the medicament. This renders the G-CSF liquid formulations according to the present invention suitable and advantageous for the use in ready-to-use syringes and kits provided therewith, in particular for home use.

The liquid formulations according to the present invention further have the advantage of preferably being free of protein-like or polymeric excipients, the use of which can be problematic from a medical point of view. As shown by the clinical studies illustrated in the Examples, they further have the advantage of being well acceptable and applicable in a substantially pain-free manner. Moreover, the G-CSF liquid formulation according to the present invention is preferably free of amino acids and/or additional proteins, such as serum albumin. In one embodiment, the liquid formulation according to the present invention is free of methionine.

It is a further advantage that it turned out in biochemical experiments and clinical studies that, due to the selection of the buffer substance in a specific range of concentration and the presence of the sugar alcohol, small amounts of surfactant from about 0.04 to 0.06 mg/ml are sufficient for stabilizing G-CSF on the one hand and do not trigger substantial skin irritations or other incompatibilities in the patient on the other hand. This is particularly advantageous in such liquid dosage forms that are intended for subcutaneous application. Moreover, by means of the measures according to the present invention, particularly the labile, non-glycosylated G-CSF molecules are sufficiently stabilized for pharmaceutical compositions. The targeted selection of excipients altogether provides very well acceptable G-CSF-containing liquid dosage forms which are high-quality preparations in terms of protein stability and are particularly suitable as ready-to-use injection or infusion solutions.

In the liquid formulations according to the present invention, amounts of surfactant in a range from 0.05 to 0.06 mg/ml, particularly preferred about 0.06 mg/ml will be used. The surfactant to be used is preferably polysorbate, particularly preferably polysorbate 80, also known as Tween 80.

The G-CSF-containing dosage forms according to the present invention contain the agent in an amount that is sufficient for achieving a therapeutic effect. Normally, agent concentrations ranging from 0.01 to 5 mg/ml are used, preferably 0.1 to 1 mg/ml, 0.3 to 0.8 mg/ml, and particularly preferred a concentration of about 0.6 mg/ml is used. In particular in case of a subcutaneous application, dosages of 0.3 mg/0.5 ml and 0.48 mg/0.8 ml turned out to be particularly preferable.

In accordance with the present invention, acetic acid is employed as a buffer substance. In the preparation of the liquid formulation according to the present invention, the buffer substance is provided in form of its free acid. The desired pH value of the solution is adjusted by the addition of bases, like for example alkali hydroxides, earth alkali hydroxides or ammonium hydroxide. For this purpose, the use of sodium hydroxide is preferred.

The concentrations of the buffer substance acetic acid in the ready-to-use liquid dosage form range from about 5 to 20 mMol/l. For the sake of simplification, it will be referred to the anion concentrations of said acid, i.e. acetate, in the following. The term acetate is intended to also comprise undissociated acetic acid. Preferably, the following buffer concentrations and pH values are employed: 7.5 to 15 mMol, particularly preferably 10 mMol acetate and pH 4.1 to 4.4; preferably pH 4.15 to 4.3; and in particular pH 4.2.

The G-CSF used in the liquid formulations according to the present invention basically relates to all G-CSF molecules produced by means of recombinant methods as well as to variations thereof. The term G-CSF or G-CSF variant according to the present invention includes all naturally occurring variants of G-CSF as well as G-CSF proteins derived therefrom and modified by means of recombinant DNA technology, in particular fusion proteins also containing other protein sequences besides the G-CSF portion. Particularly preferred in this sense is a G-CSF mutein having an N-terminal Met residue at position-1, which is generated by the expression in prokaryotic cells. Also suitable is a recombinant methionine-free G-CSF variant that can be produced according to WO 91/11520. The term "G-CSF variant" is understood to denote such G-CSF molecules in which one or more amino acids can be deleted or substituted by other amino acids, wherein the substantial characteristics of G-CSF are maintained to a large extent. Suitable G-CSF muteins are described, for example, in EP 0 456 200. Particularly preferred, the G-CSF that is present in the liquid formulations according to the present invention is not glycosylated.

For the preparation of well acceptable parenteral dosage forms the admixture of isotonizing excipients is appropriate, unless isotonia can already be achieved with the osmotic properties of the agent and of the excipients employed for stabilizing. To this end, particularly non-ionized, well acceptable excipients, like for example mannitol, glycerol or other sugar alcohols, are employed. In case of G-CSF the use of sorbitol is preferred, which is particularly advantageous for the acceptability of the liquid formulations according to the present invention. Preferably, the sugar alcohol is present in the liquid formulation at a concentration ranging from about 2.5 to 7.5% (w/v), particularly preferably at a concentration of about 5% (w/v).

The admixture of salts for adjusting isotonia is not advantageous as high concentrations of salt or ions enhance the aggregate formation of G-CSF. Therefore, salts are advantageously admixed in small amounts. The buffer concentrations are measured in such a way that the pH-stabilizing effect is achieved while the ionic strength is kept at the lowest possible level. Preferably, the buffer concentrations are within a range of up to 20 mMol, in particular less than 15 mMol.

Moreover, the ready-to-use injection solutions may contain further conventional excipients or additives. Antioxidants, like for example glutathione, ascorbic acid or similar substances, chaotropic excipients, like for example urea, or amino acids, like for example methionine, arginine, lysine, ornithine and the like, can be admixed.

In a particularly preferred embodiment, the aqueous liquid formulation of G-CSF according to the present invention is prepared in form of an injection or infusion solution and substantially consists of human, non-glycosylated methionyl-G-CSF at a concentration of about 0.6 mg/ml and sorbitol at a concentration of about 5% (w/v), polysorbate 80 at a concentration of about 0.06 mg/ml, and acetate at a concentration of about 10 mM as a buffer substance at a pH value of about 4.2.

In other respects and with the same dosage strength, the liquid formulations of G-CSF according to the present invention can be used according to the product information of Neupogen®, in particular with regard to dosage, administration and medical indication, as the use of highly purified, non-glycosylated G-CSF protein like filgrastim, which is produced in a laboratory strain of $E.$ $coli$ K12, is also preferred in liquid formulations according to the present invention.

The liquid formulations according to the present invention are advantageously used as a medicament for the treatment of diseases that are known to be treatable by administration of G-CSF, like cancer, adverse side effects caused by cytotoxic chemotherapy, accompanying therapy of diseases, wherein a mobilization of peripheral blood precursor cells is required, severe chronic neutropenia (SCN), HIV infection, and the like. Accordingly, the present invention in particular relates to medicaments comprising one of the G-CSF liquid formulations described above.

In one embodiment, the G-CSF composition according to the present invention is intended for the preparation of a medicament for the treatment of neurological indications, like a damage of the central nervous system, for example subsequent to an acute cerebrovascular accident, wherein severe secondary damages can be alleviated or prevented by means of early administration, for example in form of a bolus. In other respects, the liquid formulations according to the present invention are intended as a medicament, preferably for subcutaneous or intravenous administration, for example by injection with prefilled syringes or by infusion, in case a long-term continuous administration of G-CSF is desirable.

As already illustrated above, the liquid formulation of G-CSF according to the present invention is stable over a long time period and can basically be stored in any suitable receptacle. Accordingly, the present invention also relates to a receptacle containing one of the liquid formulations of G-CSF described above or in the Examples. Preferably, at least one surface of the receptacle which is in contact with the liquid formulation is coated with a material consisting of polytetrafluoroethylene or ethylene-tetrafluoroethylene (ETFE). Typically, the receptacle is a container that is conventionally intended for the storage and/or administration of a liquid medicament, like a vial, a syringe, an ampoule, a carpoule, or an infusion container, wherein the liquid formulation of G-CSF according to the present invention is particularly advantageous for the use in ready-to-use syringes and ampoules. In a preferred embodiment, the liquid formulation is present in the syringe or in the ampoule at a concentration, in terms of concentration of G-CSF, of 0.3 mg in 0.5 ml or 0.48 mg in 0.8 ml.

As admixing further excipients or taking further preparatory measures, like filtering, mixing, etc., prior to the administration of the liquid formulation of G-CSF according to the present invention can advantageously be omitted, the G-CSF liquid medicament according to the present invention can be prepared for immediate administration, for example in a kit.

In an embodiment that is particularly advantageous for physicians, pharmacists and especially for patients, the present invention therefore also relates to a kit for the parenteral administration of G-CSF, comprising one or more of the above-described receptacles, preferably along with instructions for storage and/or administration. Usually, the administration of G-CSF at a dosage of 5 to 30 μg/kg body weight will be provided, wherein higher or lower dosages may be indicated, however, depending on the medical indication and the stage of the disease.

Preferably, 5 syringes or ampoules are provided in the kit according to the present invention, optionally more, like 7 syringes or ampoules, for example in case the daily administration is intended to last for one week.

For reasons of safe handling, the kit according to the present invention advantageously has safety compartments for syringes and for injection and/or infusion needles, respectively. Here, discharge aids for the needles and prepared or pre-fitted sealing caps are also to be considered.

As is described in the Examples, the G-CSF liquid formulations according to the present invention are stable over a long time period, in particular at about 5° C., preferably over a period of at least 4 weeks. Therefore, the liquid formulations, receptacles and kits according to the present invention can advantageously be stored in a conventional refrigerator.

These and further embodiments resulting from the present invention are encompassed by the claims. The disclosure of the prior art documents cited above and in the following is herewith incorporated in the present application by reference, in particular with respect to the recombinant production of G-CSF, buffers, syringes and kits. These and further embodiments are disclosed and apparent to the person skilled in the art and are encompassed by the description and the Examples of the present invention. Further literature on one of the above-mentioned excipients as well as on electronic means that can be used in accordance with the present invention can be taken from the prior art, for example from public libraries using, e.g., electronic means. In addition, further public databases are readily available via the internet, like for example "PubMed" (pubmed.gov).

Techniques for performing the present invention are known to the person skilled in the art and can be taken from the relevant literature, see for example Molecular Cloning A Laboratory Manual, 2nd Ed., ed. by Sambrook, Fritsch and Maniatis (Cold Spring Harbor Laboratory Press: 1989); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986).

EXAMPLES

In the following, the present invention is further illustrated by way of a preferred embodiment, which is, however, not intended to limit the object of the present invention in any way.

Example 1

Preparation of the Liquid G-CSF Formulations

The solutions of G-CSF used in the Examples were prepared by dissolving the above-described excipients in water for injection purposes, adding the indicated amounts of G-CSF and, if required, exactly adjusting the pH value to the desired value using a small amount of buffer component.

When preparing the G-CSF formulation according to the present invention it is to be noted that for adjusting the acetate buffer it is required to initially provide acetic acid and to subsequently adjust the pH value using an NaOH solution, as it turned out in the process of previously conducted experiments that the use of sodium acetate with subsequently adjusting the pH value using HCl could result in the formation of protein aggregates, possibly due to an increased ion concentration.

already a lower surfactant concentration, but in any case a high surfactant concentration, negatively influences the oxidation profile of G-CSF in solution.

TABLE 1 pH values in liquid formulations having a dosage strength of 30 MIU,
0.6 mg/ml, 0.5 ml/ampoule during storage for 4 weeks at +40° C. and +5° C.

| Notation | Description of composition | Initial value +5° C. pH | 1st week at +40° C. pH | 2nd week at +40° C. pH | $4^{th}$ week at +40° C. pH | 4th week at +5° C. pH |
|---|---|---|---|---|---|---|
| I | 10 mM acetic acid, pH 4.1; 5% sorbitol, 0.004% polysorbate 80 | 4.05 | 4.08 | 4.10 | 4.12 | 4.07 |
| IIa | 10 mM acetic acid, pH 4.2; 5% sorbitol; 0.004% polysorbate 80 | 4.23 | 4.24 | 4.24 | 4.25 | 4.23 |
| IIb | 10 mM acetic acid, pH 4.3; 5% sorbitol; 0.004% polysorbate 80 | 4.33 | 4.35 | 4.34 | 4.36 | 4.33 |
| IIc | 10 mM acetic acid, pH 4.4; 5% sorbitol; 0.004% polysorbate 80 | 4.43 | 4.45 | 4.43 | 4.47 | 4.43 |
| IIIa | 10 mM acetic acid, pH 4.2; 5% sorbitol; 0.006% polysorbate 80 | 4.24 | 4.24 | 4.24 | 4.27 | 4.23 |
| IIIb | 10 mM acetic acid, pH 4.3; 5% sorbitol; 0.006% polysorbate 80 | 4.34 | 4.34 | 4.35 | 4.37 | 4.33 |
| IIIc | 10 mM acetic acid, pH 4.4; 5% sorbitol; 0.006% polysorbate 80 | 4.43 | 4.45 | 4.43 | 4.47 | 4.43 |
| IVa | 10 mM acetic acid, pH 4.2; 5% sorbitol; 0.008% polysorbate 80 | 4.21 | 4.24 | 4.22 | 4.25 | 4.21 |
| IVb | 10 mM acetic acid, pH 4.3; 5% sorbitol; 0.008% polysorbate 80 | 4.33 | 4.33 | 4.34 | 4.36 | 4.31 |
| IVc | 10 mM acetic acid, pH 4.4; 5% sorbitol; 0.008% polysorbate 80 | 4.43 | 4.45 | 4.43 | 4.45 | 4.41 |

The solutions are subsequently filtered through suitable sterilized membrane filters having a pore width of 0.2 μm, filled in sterilized glass injection vials of hydrolytic class I and sealed with sterilized teflonized rubber plugs. Filling is preferably performed in nitrogen atmosphere.

Example 2

Biochemical Stability of the G-CSF Formulations of the Present Invention

The experimental preparations of G-CSF are stored in sealed and crimped vials under exclusion of light at defined storage temperatures and subsequently tested for protein purity and the occurrence of oxidized forms, aggregates and dimers using standard techniques like UV spectroscopy, reversed-phase HPLC with C4 and C18 stationary phase, or size exclusion chromatography (SEC HPLC), isoelectric focusing, SDS-PAGE under thiol reducing and non-reducing conditions with subsequent silver staining and Western immunoblot analyses; for information on the techniques mentioned see, e.g., the examples of WO 94/14466, the disclosure of which is incorporated herein by reference.

The liquid formulations of G-CSF as specified in Table 1 of Example 1 were tested for their long-term stability, as indicated. For the formulations having a surfactant content>0.006% only the formulation with 0.008% is indicated by way of example, as formulations having a higher content of surfactant exhibit an even substantially poorer long-term stability. In experiments with respect to the biochemical stability of G-CSF in the experimental compositions it turned out that with the use of higher surfactant concentrations down to and including a content of 0.008% an accumulation of the oxidized form of G-CSF in large amounts could be observed. Therefore, it was assessed in the experiments conducted within the scope of the present invention, in contrast to the teachings of the international application WO 94/14466, that Furthermore, it was ascertained that the G-CSF formulations of the present invention as specified in Table 1 are characterized in that the relative content of oxidized species is below 1%, while this threshold value was exceeded in the control samples having a surfactant content of 0.008% and more, which leads to the conclusion that such solutions cannot be considered as candidate medicaments.

Further examinations of the biochemical stability of G-CSF in the experimental compositions revealed that the formulations according to the present invention are capable of substantially preventing both aggregation and oxidation of G-CSF without the need for further admixture of excipients like amino acids and/or antioxidants.

Example 3

Acceptability of the G-CSF Formulations

One of the liquid formulations according to the present invention was tested in three phase III clinical studies in cancer patients, wherein, inter alia, the patients' reactions in the vicinity of the injection site were examined. Here, an examination of swelling, redness, skin bleeding, sensitivity to pressure and other symptoms occurring at the injection site was performed. For the clinical studies, the G-CSF formulation of the present invention was selected according to the indications of experimental preparation IIa (XM02) in Table 1 and was processed at a dosage of 5 μg/kg body eight per day.

In the course of these examinations it fortunately turned out that only one patient out of a total number of 356 patients reported undesired reactions, i.e. in only 0.3% of the cases.

In control experiments conducted with the commercially available G-CSF formulation of Neupogen® it could be demonstrated that the G-CSF formulation of the present invention shows an acceptability that is improved by the factor 4 with respect to side effects at the injection sites in patients. These results are summarized in the following table.

TABLE 2

Frequency of reactions at the injection site in three phase III clinical studies. Evaluation of the first cycle of chemotherapy of breast cancer, Non-Hodgkin's Lymphoma and lung cancer

| Medication | pH | Total number | Positive | % Positive |
|---|---|---|---|---|
| XM02 | 4.2 | 356 | 1 | 0.3 |
| Neupogen ® | 4.0 | 249 | 3 | 1.2 |
| Placebo | 7.0 | 72 | 0 | 0.0 |

The above-mentioned examinations led to the result that by combining acetic acid and acetate, respectively, as a buffer substance and a surfactant such as polysorbate 80, each at a specific concentration and in the presence of a sugar alcohol such as sorbitol, and with adjusting the pH value to about 4.2±0.15, a stable liquid formulation of G-CSF is obtained, which conveys to the G-CSF molecules the stability required for their suitability as a medicament, is well tolerable and additionally allows for an almost complete prevention of symptoms that can often be observed at the injection site when administering the medicament. This renders the G-CSF liquid formulations according to the present invention and kits provided therewith, respectively, particularly suitable and advantageous for the use in ready-to-use syringes and kits provided therewith, in particular for home use.

The invention claimed is:

1. A medicament comprising an aqueous liquid formulation of G-CSF, the aqueous liquid formulation of G-CSF comprising G-CSF, sorbitol at a concentration of 5% w/v, polysorbate at a concentration of 0.05 to 0.06 mg/ml, and acetate at a concentration of 10 mM as a buffer substance at a pH value of 4.15 to 4.3.

2. A medicament according to claim 1, wherein the G-CSF is non-glycosylated.

3. A medicament according to claim 1, wherein the G-CSF is present at a concentration of 0.6 mg/ml.

4. A medicament according to claim 1, which is substantially free of amino acids and/or additional protein.

5. A medicament according to claim 1, which is an injection or infusion solution.

6. A medicament comprising an aqueous liquid formulation of G-CSF as injection or infusion solution, the aqueous liquid formulation of G-CSF consisting of human, non-glycosylated methionyl G-CSF at a concentration of 0.6 mg/ml and of sorbitol at a concentration of 5% (w/v), polysorbate 80 at a concentration of 0.05 to 0.06 mg/ml, and acetate at a concentration of 10 mM as a buffer substance at a pH value of 4.2±0.15.

7. A medicament according to claim 1, for the treatment of cancer, severe chronic neutropenia (SCN), HIV infection, a damage of the central nervous system, adverse side effects owing to cytotoxic chemotherapy, or for the accompanying therapy of diseases, wherein a mobilization of peripheral blood precursor cells is required.

8. A receptacle for the administration of liquid medicaments, comprising a liquid medicament formulation according to claim 1.

9. A receptacle according to claim 8, wherein at least one surface of said receptacle, which is in contact with the liquid formulation, is coated with a material consisting of silicone or polytetrafluoroethylene or an ethylene-tetrafluoroethylene (ETFE) copolymer.

10. A receptacle according to claim 8, which is a syringe, an ampoule, a carpoule, or an infusion container.

11. The receptacle according to claim 10, wherein the receptacle is a syringe or an ampoule, and wherein the liquid formulation is present, in terms of the concentration of G-CSF, at a concentration of 0.3 mg in a 0.5 ml or 0.48 mg in 0.8 ml.

12. A kit for the parenteral administration of G-CSF, comprising a receptacle according to claim 8 as well as instructions for storage and/or administration.

13. A kit according to claim 12, wherein the administration of G-CSF is provided at a dosage of 5 to 30 μg/kg body weight.

14. A kit according to claim 12, wherein 5 syringes or ampoules are provided in said kit.

15. A kit according to claim 12, further comprising safety compartments for syringes and injection and/or infusion needles, respectively.

16. A kit according to claim 12, wherein storage is intended at 5° C.

17. A medicament according to claim 1, wherein the buffer substance is provided in the form of its free acid and the pH value of the solution is adjusted by the addition of a base.

18. A medicament according to claim 6, wherein the medicament contains less than 1% oxidized species after storage for 4 weeks at 40° C. or 5° C.

19. A. medicament according to claim 1, wherein the G-CSF is non-glycosylated and present at a concentration of 0.6 mg/ml and the pH value is 4.2 and wherein the medicament is substantially free of amino acids and/or additional proteins.

20. A receptacle for the administration of liquid medicaments, comprising the medicament according to claim 17.

21. A receptacle according to claim 20, wherein the receptacle is a syringe or an ampoule, and wherein the liquid formulation is present, in terms of the concentration of G-CSF, at a concentration of 0.3 mg in 0.5 ml or 0.48 mg in 0.8 ml.

22. The receptacle according to claim 21, wherein at least one surface of said receptacle, which is in contact with the liquid formulation, is coated with a material consisting of silicone or polytetrafluoroethylene or an ethylene-tetrafluoroethylene (ETFE) copolymer.

23. A kit for the parentaral administration of G-CSF, comprising a receptacle according to claim 22 as well as instructions for storage and/or administration.

24. The medicament of claim 1, further comprising an amino acid, glycerol, a carbohydrate, and/or a preservative.

25. A medicament according to claim 1, wherein the medicament contains less than 1% oxidized species after storage for 4 weeks at 40° C. or 5° C.

* * * * *

UNITED STATES PATENT AND TRADEMARK OFFICE
CERTIFICATE OF CORRECTION

PATENT NO. : 8,562,967 B2  
APPLICATION NO. : 12/675776  
DATED : October 22, 2013  
INVENTOR(S) : Hinderer et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 282 days.

Signed and Sealed this  
Thirty-first Day of March, 2015

Michelle K. Lee  
*Director of the United States Patent and Trademark Office*